United States Patent

Nagel et al.

Patent Number: 5,548,000
Date of Patent: Aug. 20, 1996

[54] ARTIFICIAL TOOTH

[75] Inventors: Joachim Nagel, Friedrichsdorf; Albert Erdrich, Bad Nauheim, both of Germany

[73] Assignee: Heraeus Kulzer GmbH, Hanau, Germany

[21] Appl. No.: 410,143

[22] Filed: Mar. 23, 1995

[30] Foreign Application Priority Data

Apr. 14, 1994 [DE] Germany .......................... 44 12 831.2

[51] Int. Cl.$^6$ .......................... A61C 13/087; C08K 3/36; C08K 9/06; C08L 33/10
[52] U.S. Cl. .......................... 523/115; 523/212; 523/220; 524/450; 524/493; 524/561; 433/229
[58] Field of Search .................... 523/115, 220, 523/212; 524/450, 493, 561; 433/229

[56] References Cited

U.S. PATENT DOCUMENTS

| | | | |
|---|---|---|---|
| 3,066,112 | 11/1962 | Bowen | 523/116 |
| 4,029,632 | 6/1977 | Gross et al. | 523/212 |
| 4,383,826 | 5/1983 | Butler et al. | 523/115 |
| 4,394,465 | 7/1983 | Podszun et al. | 523/220 |
| 4,407,984 | 10/1983 | Ratcliffe et al. | 523/115 |
| 4,547,531 | 10/1985 | Waknine | 523/116 |
| 4,649,165 | 3/1987 | Kuhlmann | 523/117 |
| 5,009,597 | 4/1991 | Schaefer | 523/115 |
| 5,228,907 | 7/1993 | Eppinger et al. | 523/115 |

FOREIGN PATENT DOCUMENTS

| | | |
|---|---|---|
| 0475239 | 3/1992 | European Pat. Off. . |
| 2312258 | 10/1973 | Germany . |
| 2405578 | 8/1975 | Germany . |
| 2462271 | 9/1976 | Germany . |
| 3826233 | 10/1989 | Germany . |
| 4029230 | 3/1992 | Germany . |
| 4110612 | 5/1992 | Germany . |
| 1428165 | 3/1976 | United Kingdom . |
| WO81/02254 | 8/1981 | WIPO . |

OTHER PUBLICATIONS

Chemical Abstracts, vol. 83, 1975.
Taschenbuch, Translation of p. 91, paraghraph 2 (1978).
R. Marxkors/H. Meiners, "Taschenbuch derzahnärztlichen Werkstoffkunde", [Handbook of Dental Materials], First Edition, 1978, Carl Hanser Verlag, Munich, p. 91.

Primary Examiner—Paul R. Michl
Assistant Examiner—Andrew E. C. Merriam
Attorney, Agent, or Firm—Frishauf, Holtz, Goodman, Langer & Chick, P.C.

[57] ABSTRACT

An artificial tooth of polymethacrylate, barium aluminum silicate glass and microfine silicon dioxide is described that imitates the natural tooth in its essential properties, namely mechanical strength and abrasion performance as well as transparency and depth of color. The tooth contains 15 to 35 weight % polymethacrylate, 35 to 75 weight % barium aluminum silicate glass with a mean particle size of from 0.1 to 5 micrometers, and 5 to 25 weight % silicon dioxide with a mean particle size of from 0.01 to 0.2 micrometers. In addition pigments necessary to match cosmetic requirements, are normally added as necessary.

7 Claims, No Drawings

ARTIFICIAL TOOTH

BACKGROUND OF THE INVENTION

The invention relates to an artificial tooth that contains polymethacrylate, barium aluminum silicate glass and microfine silicon dioxide.

Ceramic teeth and plastic (resin) teeth are used to produce tooth prostheses.

Plastic (resin) teeth that are based on polymethacrylate resins are well-known. These can be prepared by polymerization of mixtures of polymeric and monomeric methyl methacrylate and optionally methacrylic acid esters with multivalent alcohols acting as cross-linking agents by the so-called powder/liquid process (R. Marxkors and H. Meiners, Taschenbuch der zahnärztlichen Werkstoffkunde [Handbook of Dental Materials], First Edition, 1978, Carl Hanser Verlag, Munich, 91).

German Patent Disclosure DE 2 312 258 A discloses abrasion-proof, polishable materials and artificial teeth made from them, comprising a polymer matrix and fine-particle inorganic filler (macrofiller) dispersed in it. The filler comprises glass and/or ceramic with a minimum size of 0.8 to 8 micrometers and a maximum size of 3 to 20 micrometers. To form the polymer matrix by the powder/liquid process, powdered homo- and copolymers of methacrylic ester, and liquid monomers, such as methyl methacrylate, butyl acrylate, polyethylene glycol dimethacrylate and bisphenol-A-dimethacrylate, are used.

German Patent DE 24 62 271 C describes molded dental elements, especially artificial teeth and tooth replacement elements, that comprise polymers of acrylate or methacrylate and microfine silicon dioxide (microfillers). The microfine silicon dioxide, with a particle size of from 10 to 400 nanometers, is silanized, for instance by treatment with 3-methacryloyloxypropyltrimethoxysilane, and may be contained in the molded elements in an amount of 20 to 80 weight %. However, it has been found that plastic teeth that contain microfine silicon dioxide have a tendency to accumulate plaque. Moreover, they are not adequately resistant to compressive strain; as a result, crazing occurs, which causes discoloration and premature abrasion, and the teeth can break.

German Patent DE 24 05 578 C discloses preparing at least the outer layer of artificial teeth from a material that in addition to esters of methacrylic acid contains from 30 to 80 weight % of an inorganic filler comprising a mixture of amorphous silicic acid, produced by flame hydrolysis, and fine-particle glass, such as barium aluminum silicate glass. The proportion of this glass may make up to 25 weight % of the filler mixture.

German Patent DE 38 26 233 C proposes a composite tooth replacement element for the provision of crowns and bridges and for inlays and the like, comprising a core with high bending strength and a high modulus of elasticity, and an abrasion-proof jacket with a high-gloss surface. The core and the jacket comprise acrylate or methacrylate polymer and inorganic filler, and the filler in the case of the core can comprise 80 to 90 weight % barium aluminum silicate glass with a mean particle size of from 0.7 to 10 micrometers and from 10 to 20 weight % of highly dispersed silicon dioxide with a mean particle size of from 0.01 to 0.4 micrometers. The core contains from 30 to 90 weight % of the filler. The plastic of the core and the jacket is preferably a polymer of bis-(4-(2-hydroxy-3-methacryloyloxypropoxy)phenyl)dimethylmethane (so-called bis-GMA or Bowen monomer, U.S. Pat. No. 3,066,112 to Bowen), ethoxylated bisphenol-A-diacrylate, ethoxylated bisphenol-A-dimethacrylate, triethylene glycol dimethacrylate, dodecandiol dimethacrylate, urethane dimethacrylate from 2-hydroxyethyl methacrylate and 2,2,4-trimethylhexamethylene diisocyanate, bis-(acryloyloxymethyl)tricyclo(5,2,1,0$^{2,6}$)decane and/or bis-(methacryloyloxymethyl)tricyclo(5,2,1,0$^{2,6}$)decane.

German Patent Disclosure DE 40 29 230 A relates to a dental material based on polymerizable monomers as a binder, which contain from 20 to 90 weight % of a filler mixture of amorphous beadlike silicon dioxide particles and up to 20 mol % of an oxide of at least one element of groups I, II, III and IV with a mean primary particle size of from 0.1 to 1.0 micrometers; powdered quartz, glass ceramic or glass having a mean particle size of 0.5 to 5.0 micrometers; and optionally a microfiller for adjusting the viscosity. The addition of dibenzoyl peroxide, for example, to this dental material produces a hot-polymerizable material for making inlays and artificial teeth. The transparency and polishability are considered to be quite good.

A dental material that contains both conventional inorganic fillers (macrofillers) and microfine inorganic fillers—for which the term "hybrid composite" has come to be conventionally used—is described for example in International Patent Application WO 81/02254. It contains a filler mixture of hydrophobic silicon dioxide, with a diameter of from 0.01 to 0.04 microns, and glass, such as radiopaque glass containing barium or strontium, with a diameter of 2 to 30 microns. Bis-GMA or ethoxylated bisphenol-A-dimethacrylate and triethylene glycol dimethacrylate serve as the polymerizable monomers. The material is used as a tooth filling material and for veneering gold crowns, made for example by casting.

A dental material curable by photopolymerization is known from German Patent Disclosure DE 41 10 612 A; it essentially comprises from 10 to 60 weight % bis-(4-(2-hydroxy-3-methacryloyloxypropoxy)phenyl)dimethylmethane, triethylene glycol dimethacrylate and/or the diurethane dimethacrylate of 2,2,4-trimethylhexamethylene diisocyanate and 2-hydroxyethyl methacrylate, from 37 to 87 weight % of a filler mixture comprising from 80 to 90 weight % barium aluminum silicate glass, with a mean particle size of 0.5 to 1.5 micrometers, and 10 to 20 weight % microfine silicon dioxide, with a mean particle size of from 0.04 to 0.06 micrometers, from 0.02 to 2 weight % α-diketone, and 0.1 to 1 weight % amine. From this dental material, radiopaque abrasion-proof tooth fillings and inlays that can be polished to a high gloss can be prepared.

BRIEF DESCRIPTION OF THE DISCLOSURE

The object of the invention is to provide an artificial tooth of the type characterized above, comprising methacrylate plastic and inorganic fillers, that imitates the natural tooth in its essential properties, namely mechanical strength and abrasion performance as well as transparency and depth of color.

An artificial tooth that attains this object is characterized in accordance with the invention in that it comprises as essential components:

(i) 15 to 35 weight % polymethacrylate, (ii) 35 to 75 weight % barium aluminum silicate glass with a mean particle size of from 0.1 to 5.0 micrometers, and (iii) 5 to 25 weight % silicon dioxide with a mean particle size of from 0.01 to 0.2 micrometers.

Other components include usual pigments to adjust the cosmetic characteristics of the tooth.

DESCRIPTION OF THE INVENTION

The invention will now be illustrated by a number of preferred embodiments.

The artificial tooth according to the present invention comprises, as required components:

(i) 15 to 35 weight % polymethacrylate, (ii) 35 to 75 weight % barium aluminum silicate glass with a mean particle size of from 0.1 to 5.0 micrometers, and (iii) 5 to 25 weight % silicon dioxide with a mean particle size of from 0.01 to 0.2 micrometers.

In a second preferred embodiment, an artificial tooth essentially comprises (i) 20 to 30 weight % polymethacrylate, (ii) 50 to 70 weight % barium aluminum silicate glass with a mean particle size of from 0.5 to 3 micrometers, and (iii) 5 to 15 weight % silicon dioxide with a mean particle size of from 0.04 to 0.1 micrometers. This has proved to be especially suitable.

The barium aluminum silicate glass and the silicon dioxide are preferably silanized by any usual method (see, for example, U.S. Pat. No. 3,066,112, U.S. Pat. No. 4,547,531 and U.S. Pat. No. 4,649,165). Treatment with 3-methacryloyloxypropyltrimethoxysilane, for example, has been found suitable.

In addition to the essential components to form the tooth, it is usually preferred to add a small quantity of a pigment in order to adjust the color to match other teeth in the patients' mouth. The precise mixture ratio of the ingredients that form the artificial teeth can be ascertained as usual by preliminary trials until a match of desired cosmetic requirements is accomplished. Of primary importance is the transparency and color. These are attained by the color and transparency properties of the polymethacrylate plastic and of the fillers. Of great importance as well are the physical properties which are to be attained by the finished tooth, as determined from the starting material mixture. A prerequisite for best visual properties is that the resin and the filler particles (barium silicate glass) have a similar index of refraction.

Barium Aluminum Silicate

The barium aluminum silicate glass particles required by the invention preferably have a narrow Gaussian size distribution of between 0.1 and 5 micrometers.

Polymethacrylate Copolymer

Copolymers of from 30 to 70 weight %, and preferably 30 to 50 weight %, of bis-(4-(2-hydroxy-3-methacryloyloxypropoxy)phenyl)dimethylmethane and 30 to 70 weight %, preferably 30 to 50 weight %, of triethylene glycol dimethacrylate have proven to be especially suitable. A copolymer of a mixture in which ⅔ comprises the first monomer and ⅓ comprises the second monomer has proved especially advantageous.

EXAMPLE

Composition

An artificial tooth was prepared from a mixture essentially comprising (i) 21 weight % of the polymethacrylate copolymer described above, (ii) 70 weight % barium aluminum silicate glass with a mean particle size of 0.1 to 3 micrometers, and (iii) 9 weight % silicon dioxide with a mean particle size of 0.04 micrometers (Aerosil OX50, Degussa AG). The resulting tooth has proved to be especially good.

The artificial tooth according to the present invention has an ideal combination of optical properties—transparency and color impression with an effect of color depth—and physical properties, which are quite close to those of a natural tooth. Thus, the present invention imitation of a natural tooth is successful in attaining the objects hereof.

An artificial tooth according to the invention is distinguished by a very favorable abrasion performance (7 micrometers per year), which is similar to that of natural tooth enamel (8 micrometers per year). Its physical properties are better than the known plastic (resin) teeth; the modulus of elasticity is above 12,000 MPa.

Preparation

The preparation of the artificial tooth according to the invention is done in a manner known per se, by mixing the monomers that form the polymethacrylate copolymer with the barium aluminum silicate glass, the silicon dioxide, a small quantity of a pigment additive, and a catalyst for the hot polymerization, such as dibenzoyl peroxide; placing the doughlike mixture obtained in a mold; and polymerization of the mixture under pressure at temperatures between 80° and 170° C.

The physical properties—Vickers hardness, compressive strength, bending strength, modulus of elasticity and abrasion strength, measured as abrasion in micrometers per year—of the artificial tooth according to the invention and—for comparison with it—of commercially available artificial teeth and of enamel and dentin of the natural tooth are shown in the table below.

TABLE

| TOOTH | VICKERS HARDNESS [N/mm²] | COMPRESSIVE STRENGTH [MPa] | BENDING STRENGTH [MPa] | MODULUS OF ELASTICITY [M-Pa] | ABRASION STRENGTH [μm/year] |
|---|---|---|---|---|---|
| PMMA* | 190 | 120 | 50 | 2000 | 70 |
| Cross-linked PMMA* | 220–260 | 120–150 | 65 | 3000 | 42 |
| PMMA* with coating containing aerosil | 280 | 400 | 70 | 3500 | 23 |
| Polymethacrylate | 348 | 370 | 80 | 5800 | 23 |

TABLE-continued

| TOOTH | VICKERS HARDNESS [N/mm²] | COMPRESSIVE STRENGTH [MPa] | BENDING STRENGTH [MPa] | MODULUS OF ELASTICITY [M-Pa] | ABRASION STRENGTH [μm/year] |
| --- | --- | --- | --- | --- | --- |
| containing aerosil Ceramic | 6000 | 170 | 76 | 82000 | |
| Enamel | | 400 | 10 | 48000 | 8 |
| Dentin | | 300 | 50 | 18000 | |
| Invention Example | 450 | 450 | 140 | 13000 | 7 |

*Polymethylmethacrylate

What is claimed is:

1. An artificial tooth which consists of from 15 to 35 weight % polymethacrylate, 35 to 75 weight % barium aluminum silicate glass with a mean particle size of from 0.1 to 5 micrometers, 5 to 25 weight % silicon dioxide with a mean particle size of from 0.01 to 0.2 micrometers, and, optionally, pigment; and wherein the polymethacrylate is a copolymer of a monomer mixture of ⅔ by weight bis-[4-(2-hydroxy-3-methacryloyloxypropoxy)-phenyl]dimethyl-methan and ⅓ by weight triethylene glycol dimethacrylate.

2. The artificial tooth of claim 1, consists of 20 to 30 weight % polymethacrylate, 50 to 70 weight % barium aluminum silicate glass with a mean particle size of from 0.5 to 3 micrometers, and 5 to 15 weight % silicon dioxide with a mean particle size of from 0.04 to 0.1 micrometers.

3. The artificial tooth of claim 1, wherein the barium aluminum silicate glass and the silicon dioxide are silanized.

4. The artificial tooth of claim 1 consisting of 21 weight % polymethacrylate, 70 weight % barium aluminum silicate glass with a mean particle size of from 0.1 to 3 micrometers and 9 weight % silicon dioxide with a mean particle size of 0.04 micrometers.

5. The artificial tooth of claim 3, wherein the barium aluminum silicate glass and the silicon dioxide are silanized with 3-methacryloyloxypropyltrimethoxysilane.

6. The artificial tooth of claim 4, wherein the barium aluminum silicate glass and the silicon dioxide are silanized.

7. The artificial tooth of claim 6, wherein the barium aluminum silicate glass and the silicon dioxide are silanized with 3-methacryloyloxypropyltrimethoxysilane.

* * * * *